(12) United States Patent
Jackson

(10) Patent No.: US 6,891,629 B2
(45) Date of Patent: May 10, 2005

(54) METHOD AND APPARATUS FOR DETECTING A SUBSTRATE FEATURE

(75) Inventor: John Charles Jackson, Clifton Forge, VA (US)

(73) Assignee: MeadWestvaco Corporation, Stamford, CT (US)

(*) Notice: Subject to any disclaimer, the term of this patent is extended or adjusted under 35 U.S.C. 154(b) by 145 days.

(21) Appl. No.: 10/254,279

(22) Filed: Sep. 25, 2002

(65) Prior Publication Data

US 2003/0020914 A1 Jan. 30, 2003

Related U.S. Application Data

(63) Continuation-in-part of application No. 09/343,875, filed on Jun. 30, 1999, now Pat. No. 6,483,587.

(51) Int. Cl.[7] .......................... G01N 21/84; G01N 11/04
(52) U.S. Cl. ......................... 356/630; 356/631; 356/637
(58) Field of Search ............................... 356/429–431, 356/637, 630–632

(56) References Cited

U.S. PATENT DOCUMENTS 4,357,899 A * 11/1982 Jones et al. .................. 118/665
5,745,244 A * 4/1998 Svanqvist et al. ........... 356/429

* cited by examiner

Primary Examiner—Gregory J. Toatley, Jr.
Assistant Examiner—Amanda Merlino
(74) Attorney, Agent, or Firm—Thompson Hine LLP

(57) ABSTRACT

The invention is directed to a method and apparatus for detecting a substrate feature. A sensor is secured opposite the substrate. The sensor emits a signal onto the surface of the substrate. The sensor detects the amount of signal reflected from the substrate. The sensor is programmed with the relative signal reflective properties for a surface of the substrate. The sensor compares the expected signal reflection rates for a surface of the substrate to the actual signal reflection rate. The sensor generates an output signal to an output device.

17 Claims, 3 Drawing Sheets

METHOD AND APPARATUS FOR DETECTING A SUBSTRATE FEATURE

CROSS-REFERENCE TO RELATED APPLICATIONS

This application is a continuation-in-part of U.S. application Ser. No. 09/343,875 filed on Jun. 30, 1999 now U.S. Pat. No. 6,483,587.

BACKGROUND OF THE INVENTION

1. Field of the Invention

The invention is directed to a method and apparatus for detecting a substrate feature.

2. Description of the Related Art

Substrates, such as paperboard webs, are often coated with a variety of coatings or finishes. Extrusion coating is a process where a substrate, such as paperboard or a sheet of paperboard, is coated with a fluid or liquid, such as polyethylene. Conventionally the coating is placed on the substrate using extrusion methods. A typical method uses various equipment to move the substrate under an extrusion coating apparatus. The extrusion coating apparatus sprays or dispenses the coating material onto the substrate surface. Typically, the coating extends beyond at least one of the substrate's perimeters, thereby creating an "edge bead". In many coated substrates, it is important that an edge bead exist to ensure that the entire substrate is adequately coated.

Some coating materials are difficult to control at the substrate's perimeter. These coating materials, such as polymers, are subject to occasional and unpredictable "wicking in." This occurs when the edge of the coating moves internal to the perimeter of the substrate. A typical "wicking in" can have a width of several inches or more. In addition, during a continuous coating operation the "wicking in" may continue for several seconds or longer. Often the "wicking in" will continue until corrective adjustments are made to the extrusion coating apparatus. A typical "wicking in" can leave a long section of the substrate inadequately coated. The lack of adequate coverage along the substrate perimeter is a major coating operation defect and must be quickly detected and corrected.

It is known to employ cameras to monitor substrate coating operations. However, the camera systems are expensive and operationally limited. In addition, the camera systems often require a section of the substrate to be shielded or covered for accurate monitoring.

It is also known to use photo sensors to inspect a coated substrate for a given product specification or tolerance. The photo sensors can be used to detect the location of coating edges. Exemplary of such prior art is U.S. Pat. No. 4,357,899 by Jones et al., entitled "Coating Apparatus". Jones teaches controlling a liquid coating process through reservoir design tanks and a detection system. However, the Jones' detection system is of limited utility. The Jones' system cannot be used on a conventional extrusion coating apparatus for both substrate sheets and a continuous substrate web. In addition, the Jones' system cannot detect gaps between individual sheets or detect a break in a continuous substrate web. Therefore, there exists a need for an improved method and apparatus for detecting coating on a substrate.

SUMMARY OF THE INVENTION

The invention is directed to a method and apparatus to detect a substrate feature. In an exemplary embodiment, a sensor is located opposite the substrate. The sensor directs a signal, such as light, onto the surface of the substrate. The sensor detects the amount of signal reflected from the substrate. The sensor is programmed with the relative reflective properties of the surface of the substrate. The sensor compares the expected signal reflection value for a surface area of the substrate to the actual signal reflected from the substrate. The sensor generates an output signal to an output device.

The above and other features of the invention will become more apparent and are best understood by reading the following detailed description of the invention in conjunction with the figures, wherein like characters represent like parts throughout the figures.

DETAILED DESCRIPTION OF THE INVENTION

Figure 1:
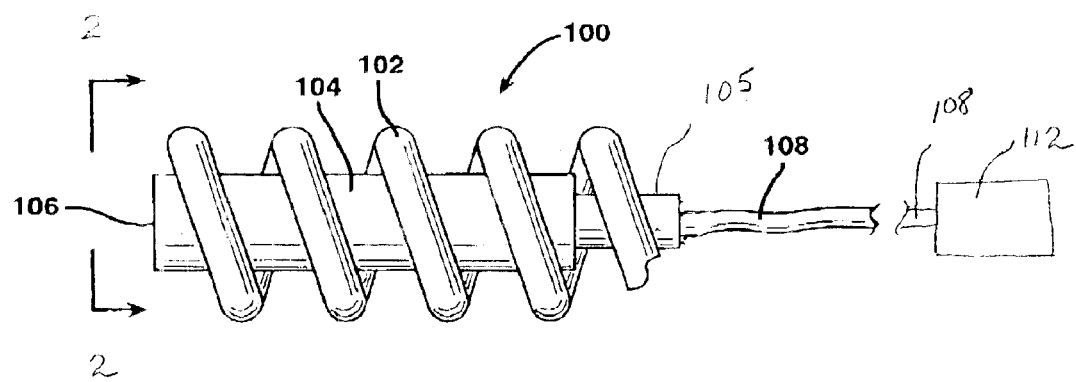
FIG. 1 illustrates a detection system according to the invention.

FIG. 1 illustrates an exemplary detection system 100. System 100 is illustrated with the following components: housing 102, bushing 104, sensor 106, sensor cable casing 105, sensor cable 108, and sensor control unit 112. In an exemplary embodiment, housing 102 is a coiled spring. Housing 102, bushing 104, and sensor cable casing 105 are made of any suitable material. The housing 102 ideally protects the sensor 106 and sensor cable 108 during detection operations. For example, when a coating process fails, such as when a substrate web breaks, the sensor 106 and sensor cable 108 are protected by the housing 102, bushing 104, and sensor cable casing 105. In addition, if the housing 102 is a spring coil, it can bring the sensor 106 back into the desired position if the sensor 106 is moved.

In an exemplary embodiment, sensor 106 is an optic sensor attached to a sensor control unit 112 via a fiber optic cable 108. The sensor 106 can detect a substrate feature such as the presence of a coating on a substrate. In addition, an exemplary sensor 106 can detect the thickness of the coating, the edge of a coating, or the edge of the substrate. An ideal optic sensor 106 can operate over a wide range of coating materials and substrate colors. A typical optic sensor 106 is capable of detecting an object of only 0.001 inch thickness. Preferably, sensor 106 is auto-reflective and self-contained. Also, the sensor 106 should ideally not require an opposing light source or separate reflector signal.

Sensor 106 is exemplary illustrated with a sensor control unit 112, however many possible sensor 106 configurations are possible. For example, the sensor 106 could be several discrete items or a combined sensor 106 and sensor control unit 112. It is further to be understood that sensor 106 may be operatively connected to multiple control units (not shown) via a plurality of sensor cables 108 (only one illustrated) or by other suitable means (not shown). An exemplary sensor control unit 112 may also be operatively connected (not shown) to a coating apparatus (not shown) or coating control unit (not shown). Furthermore, an exemplary sensor 106 and/or sensor control unit 112 generates and transmits an output signal to an output device (not shown).

It is further to be understood that sensor 106 and/or sensor control unit 112 can be connected to an optional alarm system (not shown) or other means (not shown) to alert the operator if the detection system 100 detects a substrate feature error.

Figure 2:
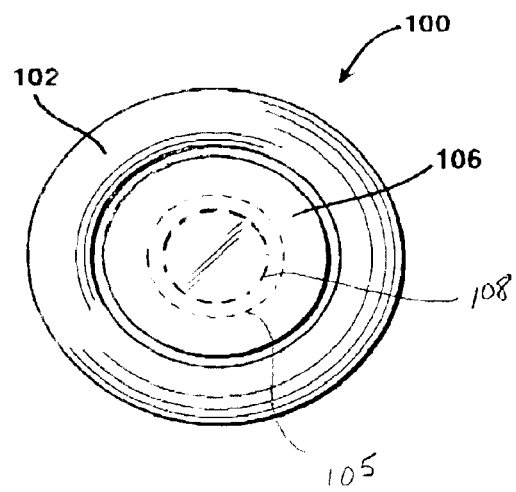
FIG. 2 is a view from line 2—2 of FIG. 1.

FIG. 2 is a view of the system 100 of FIG. 1 along line 2—2. In an exemplary embodiment, bushing 104 has an outside diameter which is slightly larger than the inside diameter of housing 102. The bushing 104 ideally fits tightly within the housing 102. Bushing 104 is illustrated with a central aperture, so that the sensor cable casing 105 and sensor cable 108 are secured within the bushing 104. Optionally, the depth that sensor 106 penetrates bushing 104 can be adjusted. In an exemplary embodiment, sensor 106 is detachable from sensor cable 108.

Figure 3:
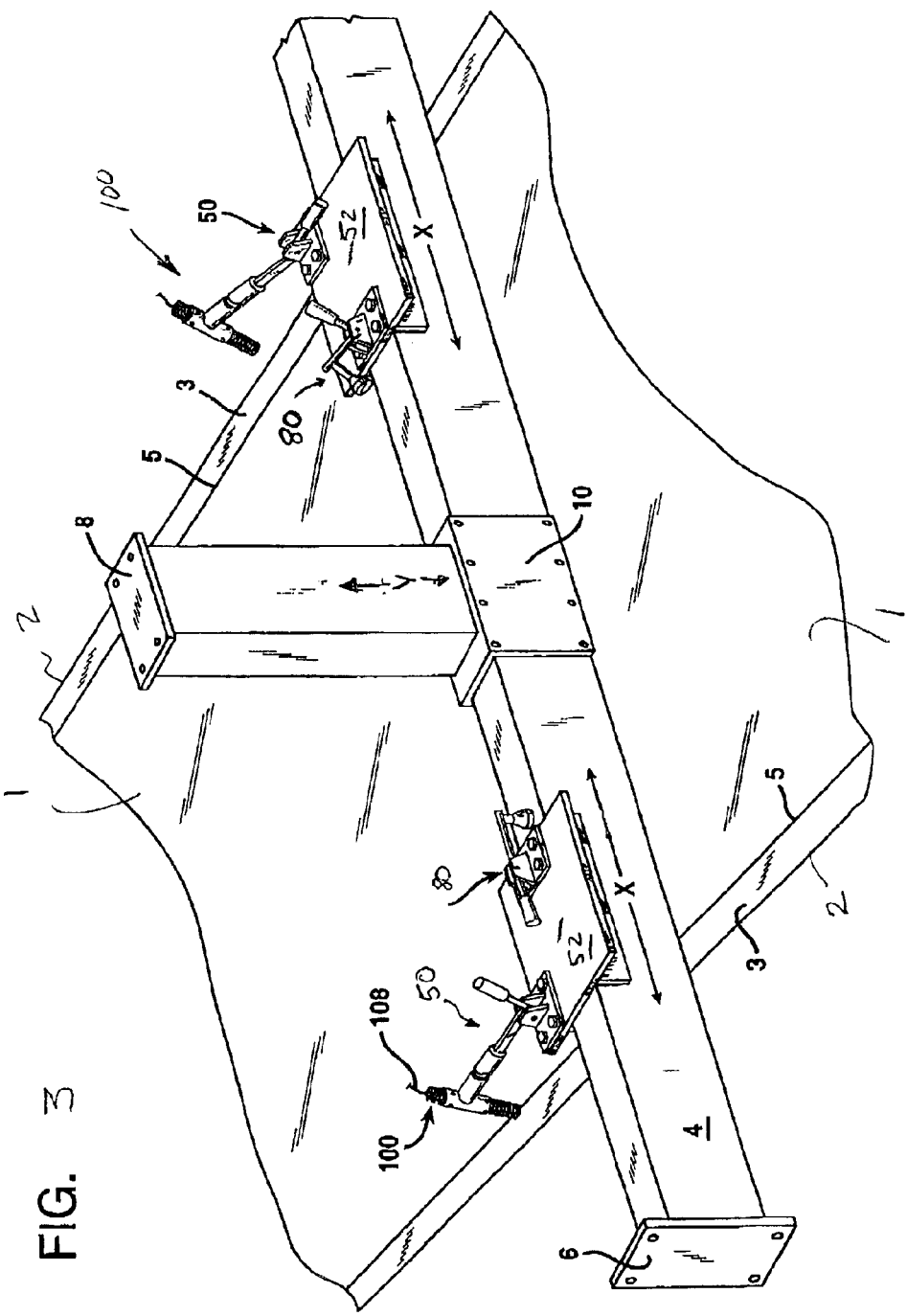
FIG. 3 illustrates an exemplary detection system environment and detection support mechanism according to the invention.

FIG. 3 illustrates an exemplary environment for use of the invention. Two detection systems 100 of FIG. 1 are shown on opposite sides of a substrate 2. The substrate 2 is illustrated with a coated area 1 and uncoated area 3. The coated area 1 is illustrated with a coating perimeter 5. It is to be understood that substrate 2 can either be a length of a substrate web or a length of a substrate sheet. The detection systems 100 are exemplary illustrated secured to frame 4 by apparatus 50 and base 52. Frame 4 is illustrated as being supported above substrate 2. Frame 4 is further illustrated with an exemplary support 6, support 8, support 10, base 52, apparatus 50, and mechanisms 80. It is to be understood that frame 4, support 6, support 8, support 10, and base 52 can be constructed of any suitable material. Supports 6, 8, and 10 and base 52 can be secured to frame 4 by conventional methods.

Figure 4:
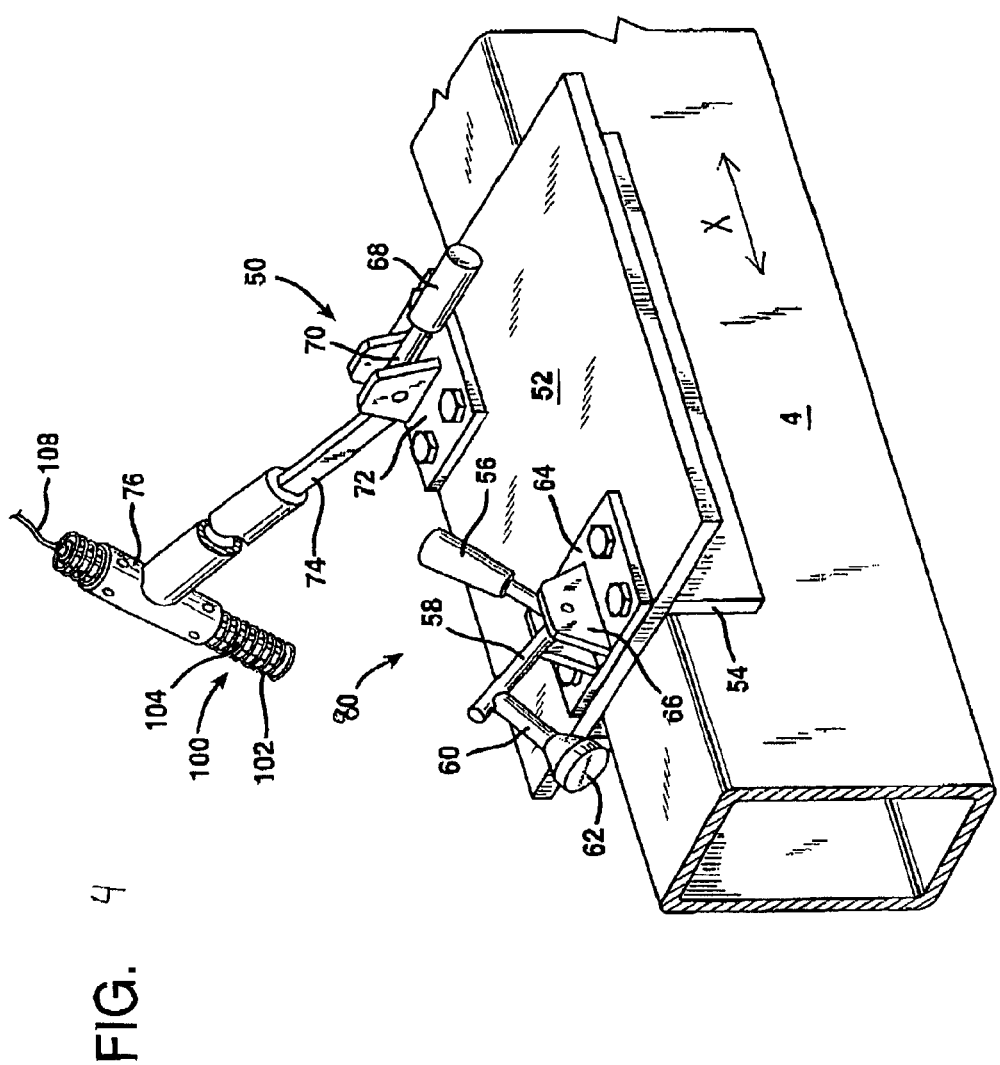
FIG. 4 further illustrates the support mechanism of FIG. 3.

FIG. 4 illustrates in detail base 52, apparatus 50, and mechanism 80. In an exemplary embodiment, base 52 and guide 54 are moveable on frame 4 in the direction of arrow X. Apparatus 50 and mechanism 80 are illustrated secured to base 52. Mechanism 80 is illustrated with arms 56 and 58, extension 60, stop 62, base 64, and support 66. Base 64 is exemplary illustrated secured to base 52. Apparatus 50 is exemplary illustrated with arms 68 and 74, pivot 70, base 72, and means 76 to secure the detection system 100. Base 72 is exemplary illustrated secured to base 52. In an exemplary arrangement, when arm 56 is parallel to frame 4, stop 62 is placed in contact with frame 4. Preferably stop 62 is constructed of a suitable material to secure base 52 at a fixed location on the frame 4. In an exemplary embodiment, when arm 68 is moved away from frame 4, the detection system 100 is moved toward substrate 2 in the direction of arrow Y (FIG. 3). It is to be understood that the above elements can be made of any suitable material and that many different configurations of base 52, apparatus 50, and mechanism 80 are possible.

In an exemplary method according to the invention, the detection system 100 is manually located over the substrate 2. The detection system 100 is located at the desired detection point, exemplary illustrated as coating perimeter 5. In an exemplary method, the detection system 100 is relocated by moving base 52 along frame 4 to the desired new position. The vertical distance (Y direction) between the detection system 100 and substrate 2 can be adjusted using apparatus 50. It is to be understood that the placement and movement of the detection system 100 can be automated using conventional methods.

In an exemplary substrate coating detection method, the detection system 100 is located at a desired distance downstream from the coating apparatus (not shown). The detection system 100 is placed at a desired location over the substrate 2. The sensor 106 emits a signal onto the surface of the substrate 2. The sensor 106 detects the amount of signal reflected from the substrate 2. Typically the coated area 1 and uncoated area 3 of the substrate 2 reflect the emitted signal at different amounts relative to each other. Using conventional means, the coating operator can program the appropriate signal reflection values for coated areas 1 and uncoated areas 3 into the sensor 106, exemplary via sensor control unit 112. The sensor 106 and sensor control unit 112 compare the amount of signal actually reflected from the surface of the substrate 2 to the amount of signal expected for a properly coated substrate surface. The sensor control unit 112 or other suitable means compares the actual and expected signal reflection rates and generates an output signal (not shown). It is to be understood that the sensor 106 and/or sensor control unit 112 may also transmit the signal data to another control unit (not shown) for further analysis. If the coating is located in the proper location, the output signal informs that the operator that the coating apparatus is operating normal. However, if the coating is not located at the desired location, the output signal informs the operator that the coating apparatus is not operating at an acceptable range.

It is to be understood that detection system 100 can be operationally connected to a wide range of output displays (not shown), such as video monitors or lighting systems and a wide range of operator alarm devices (not shown), such as buzzers or flashing lights, to alert the operator when the coating system is not operating properly. It is further to be understood that detection system 100 can be optionally connected to a conventional coater (not shown) to provide operational feedback and/or control the coater (not shown). For example, if a coating error is detected by detection system 100, an alarm may sound and the coater (not shown) may be shut down until the error is corrected or the coater may be adjusted while it operates. In addition, the sensor 106 and/or sensor control unit 112 may also recommend adjustments to the operator to correct the error. It is also to be understood that the detection system 100 may also be operatively connected to a marking apparatus (not shown), so that defective coated areas of the substrate 2 are marked for further analysis and/or disposal.

It is to be understood that although detection system 100 is described above for detecting coating areas, it can also used to detect gaps between separate substrates (not shown) or any other measurable physical or chemical substrate features using similar methods. In particular, detection system 100 is flexible and can be located in one position to detect a coating perimeter 5 and in another to detect a gap between two separate substrates. It is further to be understood that the coated surface area 1 could extend beyond the perimeter of the substrate 2 during certain exemplary extrusion processes. In such cases, the detection system 100 could be used to detect the presence of an edge bead.

Once given the above disclosure, many other features, modifications, or improvements will become apparent to the skilled artisan. Such features, modifications, or improvements are, therefore, considered to be a part of this invention, the scope of which is to be determined by the following claims:

What is claimed is:

1. A method of detecting a substrate feature comprising the steps of:

providing a substrate;

providing a frame positioned over said substrate and extending generally perpendicular to a length of said substrate;

slidably mounting at least one sensor to said frame such that said sensor may be positioned at various locations along said frame, wherein said sensor emits a known signal onto a designated area of said substrate and wherein said sensor measures the amount of signal reflected from said substrate;

said sensor being housed in a spring coil" has been added after "substrate";

programming said sensor with an acceptable signal reflection rate range for said designated area of said substrate;

comparing said signal reflected from said substrate to said acceptable signal reflection rate ranges; and generating an output signal to an output device based on said comparison.

2. The method of claim 1 wherein said signal comprise optical means.

3. The method of claim 2 wherein said sensor further comprises a means to detect optical reflections.

4. The method of claim 1 wherein said sensor is in digital communication with said output device.

5. The method of claim 1 wherein said sensor is an analog

6. The method of claim 1 wherein said sensor further comprises an input means.

7. The method of claim 1 wherein said output device further comprises a video output.

8. The method of claim 1 wherein said output device further comprises an alarm device.

9. The method of claim 1 wherein said sensor further comprises a housing apparatus.

10. The method of claim 9 wherein said housing apparatus further comprises a bushing apparatus wherein said bushing apparatus is located substantially inside said housing apparatus.

11. The method of claim 9 wherein a sensor cable is located substantially inside said bushing apparatus.

12. The method of claim 9 wherein said sensor is at least partially located inside said housing apparatus.

13. The method of claim 1 wherein said sensor is operatively secured to a mount located some distance from said substrate, wherein said mount is slidably connected to said frame.

14. The method of claim 13 wherein said mounting means further comprises a frame, a moveable base operatively secured to said frame, and a sensor mounting means secured to said moveable base and said sensor.

15. The method of claim 1 wherein said substrate feature comprises a coating on said substrate.

16. The method of claim 1 wherein said substrate feature comprises a perimeter of said substrate.

17. The method of claim 1 wherein said substrate feature comprises an edge bead secured to said substrate.

* * * * *

UNITED STATES PATENT AND TRADEMARK OFFICE
CERTIFICATE OF CORRECTION

PATENT NO. : 6,891,629 B2
DATED : May 10, 2005
INVENTOR(S) : John Charles Jackson It is certified that error appears in the above-identified patent and that said Letters Patent is hereby corrected as shown below:

Column 5,
Line 6, after "substrate" insert -- said sensor being housed in a spring coil --.
Lines 7 and 8, after "coil" delete "has been added after "substrate".
Line 13, change "ranges" to -- range --.
Line 22, after "analog" insert -- communication with said output device --.

Signed and Sealed this

Thirtieth Day of August, 2005

JON W. DUDAS
*Director of the United States Patent and Trademark Office*